United States Patent [19]

Ascher et al.

[11] Patent Number: 4,596,256

[45] Date of Patent: Jun. 24, 1986

[54] PORTABLE APPARATUS FOR RECORDING ELECTROCARDIOGRAMS

[76] Inventors: Gilles Ascher, 20bis, Boulevard du Général Leclerc, F-92200 Neuilly; Jean-Pierre Coustenoble, 11 rue Charcot, 92800 Puteaux, both of France

[21] Appl. No.: 574,009

[22] Filed: Jan. 26, 1984

[30] Foreign Application Priority Data

Feb. 4, 1983 [FR] France .................................. 83 01796

[51] Int. Cl.$^4$ ............................................... A61B 5/04
[52] U.S. Cl. ................................................... 128/710
[58] Field of Search .............. 128/639, 644, 696, 710, 128/668, 687, 688, 672

[56] References Cited

U.S. PATENT DOCUMENTS

| | | | |
|---|---|---|---|
| 3,067,749 | 12/1962 | Waltons | 128/644 |
| 3,450,133 | 6/1969 | Birch, Jr. | 128/644 |
| 3,880,145 | 4/1975 | Blick | 128/672 |
| 3,938,507 | 2/1976 | Sarnoff et al. | 128/701 |
| 4,015,596 | 4/1977 | Dehnert | 128/644 |

Primary Examiner—William E. Kamm
Attorney, Agent, or Firm—Andrus, Sceales, Starke & Sawall

[57] ABSTRACT

Portable apparatus for recording electrocardiograms registered on the patient's hands avoids the patient tensing his/her hands during the recording, so as to avoid degradation of the recording quality. A pocket-sized casing has two separate electrodes which contact parts of the respective hands of the patient. Retaining members are juxtaposed to the electrodes for pressing the hands into contact with the electrodes and maintaining the apparatus in position in the patient's hands. The apparatus is also usable for precordial electrocardiograms.

8 Claims, 5 Drawing Figures

PORTABLE APPARATUS FOR RECORDING ELECTROCARDIOGRAMS

BACKGROUND TO THE INVENTION

This invention relates to apparatus for recording electrocardiograms, of a kind enabling an electrocardiogram to be registered and recorded without specialised apparatus or particular know-how. Such apparatus enables a patient to record one or more electrocardiograms at the moment when the symptoms of a cardiac ailment appear. This offers a very simple manner in which an electrocardiogram significant to the ailment afflicting the patient to be obtained whatever the circumstances and location, without outside aids; the electrocardiograms thus registered are recorded by the apparatus and the recordings can be read and analysed subsequently by the practising doctor.

DESCRIPTION OF THE PRIOR ART

Portable apparatus for recording electrocardiograms are known in which the electrocardiogram is registered between the patient's hands. Such apparatus comprises two electrodes to which are applied one or more fingers of each hand when an ailment appears, the recording being made automatically. It has been observed that patients tend to tense their hands at the moment that the recording is being made, with resulting variations of the pressure on the electrodes, which leads to poor quality of the recordings, because of the presence of artifacts.

OBJECT OF THE INVENTION

An object of the invention is to provide a portable apparatus for registering and recording electrocardiograms of the above kind, which reduces the tendency for the patient to tense his hands during the recording, so as to improve the quality of the recording.

BRIEF DESCRIPTION OF THE INVENTION

The present invention provides portable apparatus for recording electrocardiograms from a patient's hands, comprising a pocket-sized casing, first and second electrode means for contacting at least parts of respective hands of the patient, and retaining means juxtaposed with said electrode means for pressing said parts of the patient's hands into contact with said electrode means, and maintaining said apparatus in position in the patient's hands.

The retaining means acts so that the patient does not have to exert any effort to hold his hands in contact with the electrodes, which reduces the risk of him tensing his hands. Also, the hands are maintained immobile and under constant pressure on the electrodes during the recording of the electrocardiogram. This gives a significant improvement in recording quality even in difficult recording conditions.

A preferred embodiment of the apparatus includes trigger means actuable by a further part of one of the patient's hands for triggering recording of said electrocardiogram.

Also the apparatus preferably includes transducer means for contacting at least part of one of the patient's hands and registering systolic and distolic blood pressure. This enables simultaneous recordings to be made of the electrocardiogram and of the blood pressure at the moment the symptoms appear. The analysis of the doctor will give an even more precise diagnosis.

In one embodiment of the invention, said parts and said further part of the patient's hands include the index fingers, from which said electrocardiogram is registered. One index finger may trigger the recording while blood pressure is measured on the other.

In another embodiment of the invention, said parts of the patient's hands include the index fingers, from which said electrocardiogram is registered, and said further part includes one of the patient's thumbs. The thumb then triggers the recording, while the index fingers contact the electrodes.

DESCRIPTION OF THE DRAWINGS

Other features and advantages of the invention will appear from the following description, given by way of example and with reference to the accompanying drawings in which.

Figure 1:
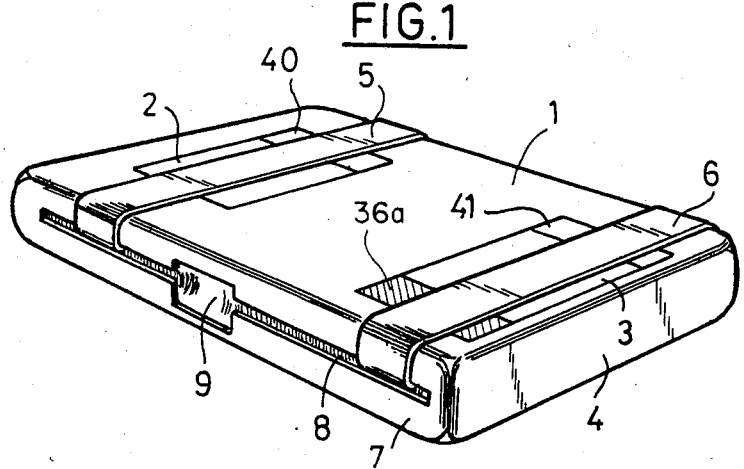
FIG. 1 is a perspective view of an apparatus in accordance with the invention.

The electrocardiogram recording apparatus shown in FIG. 1 comprises a generally flat casing 1 of size small enough to be carried in the patient's pocket; on the upper face of the casing are provided two electrocardiogram pick-up electrodes 2 and 3, which are suitable for contact with parts of the patient's hands, in this case the four fingers of each hand. To this end, the casing 1 is taken in both hands, the palm of one hand applied on the small side 4 of the casing and the palm of the other hand applied to the opposite side of the casing 1, the thumbs being placed on the lower face of the casing.

Retaining means for the parts of the hands contacting the electrodes 2 and 3 are provided; these retaining means press the relevant part of the hand onto the electrodes with a constant pressure. The patient does not have to grip the casing since his hands are maintained, and there is therefore no tendency for him to tense his hands. In the embodiment shown in FIG. 1, the retaining means are elastic, and comprise two elastic strips 5 and 6 disposed generally juxtaposed to the electrodes and extending over the whole width of the casing 1. These retaining strips 5 and 6 are secured to the two sides of the casing 1 which the patient's hands do not contact during the electrocardiogram recording.

Figure 3:
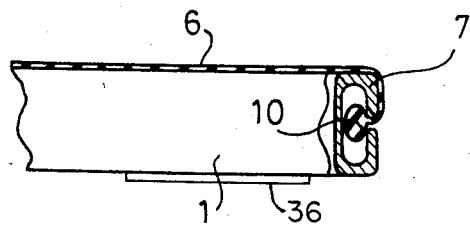

To this end, these two sides (of which only one side 7 is visible in FIG. 1) present a longitudinal dove-tail shaped slit 8, whose section is shown in FIG. 3. This longitudinal slit comprises a notch 9, preferably disposed at the middle and whose width corresponds approximately to the base of the slit 8.

Figure 2:
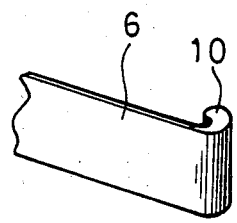
FIGS. 2 and 3 are detail views of retaining means in the apparatus of FIG. 1.

In addition, the ends of the strips 5 and 6 have an enlarged section 10 (see FIG. 2) whose section corresponds to the width of the notch 9; this enlarged section is obtained for example, by rolling up the ends of the strips 5 and 6. It will be understood that the ends 10 of the strips 5 and 6 may be engaged in the notch 9 and then slid along in the slit 8 to bring the strips 5 and 6 opposite the electrodes 2 and 3.

Figure 4:
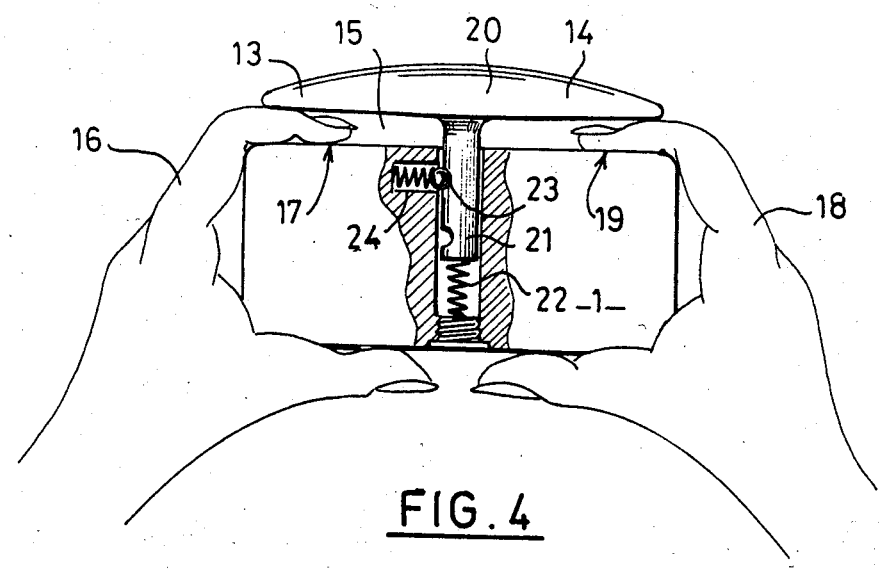
FIG. 4 is a side view of a variant of the apparatus of FIG. 1.

The apparatus shown in FIG. 4 comprises a variant of the retaining means of FIG. 1; the retaining means of FIG. 4 comprises two clamps 13 and 14 secured to one side of the casing 1; the clamps 13 and 14 are relatively elastic and form a spring which defines with the side of the casing 1 a recess 15 for receiving a finger. In this case the patient inserts a finger of each hand under the clamps 13 and 14 which press on the fingers and maintain them in place against a measurement or trigger member. In the example illustrated, one finger 16 of one hand, for example the index finger, is applied to a member 17 for triggering the electrocardiogram recording, and the other finger 18 is applied to a pick-up 19 which is suitable for measuring the systolic and the diastolic blood pressure graphs.

In the embodiment shown in FIG. 4, the two clamps 13 and 14 comprise a horizontal bar of a T-shaped part 20, whose vertical bar 21 is mounted slidingly in the casing 1. The T-shaped piece 20 is urged towards the casing 1 by a return spring device indicated schematically at 22. This retaining device comprising the T-piece 20 comprises a latch shown schematically in FIG. 4 and comprising a ball 23 urged by a spring 24 against the bar 21 and cooperating with a notch therein. Advantageously, the latch, which is provided to hold the T-piece 20 spaced from the casing 1 to enable the fingers 16 to be inserted more readily into the recesses 15, comprises an unlatching member (not shown) so as to allow the T-piece 20 to return and press the fingers of the patient in the electrocardiogram recording position. This unlatching member acts on the ball 23, for example; it may be actuated by another part of the patient's hands. Advantageously, this unlatching member may be coupled to the device for triggering the recording.

Figure 5:
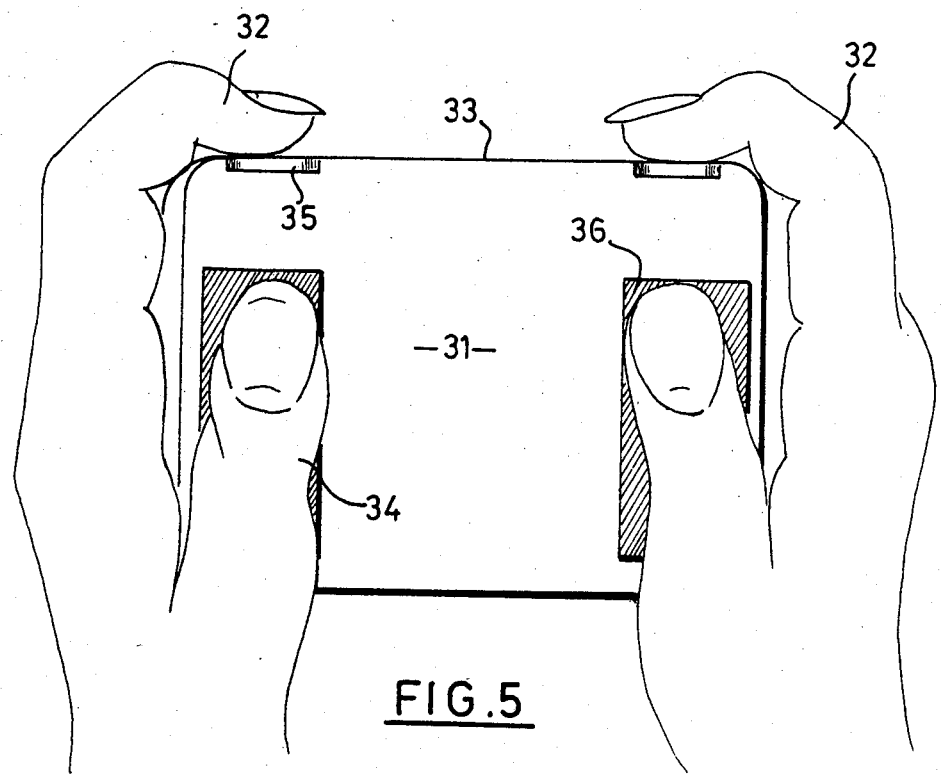
FIG. 5 is a side view of another apparatus in accordance with the invention.

FIG. 5 shows another variant of the casing 31, which has the general shape and approximate size of a packet of cigarettes. In this embodiment the electrocardiogram recording is taken from the patient's index fingers such as 32 which are applied to electrocardiogram electrodes 35 disposed on one of the long sides 33 of the casing 31, and the fingers may be retained in position by retaining means (not shown) such as that illustrated in FIG. 4 for example. At least one of the patient's thumbs, such as 34 contacts a device 36 for triggering the recording and unlatching the clamps as in the case of the retaining means shown in FIG. 4. Triggering device 36 and 36a may also be provided in the embodiment of the invention shown in FIG. 1 for actuation by the thumb or index finger of the patient. Blood pressure graphs may be measured from one of the index fingers.

Since the electrocardiogram electrodes are disposed on the longer side 33 of the casing 31, their spacing is sufficient for the apparatus to be used for precordial recording so as to refine further the characteristics of the curve recorded. For pre-cordial recording, if retaining means are provided, it must be possible for them to be disengaged to expose the electrodes, and elastic retaining strips as described with reference to FIGS. 1 to 3 may be used.

When the apparatus includes a device for recording the systolic and diasystolic blood pressure curves, it is necessary for the doctor to have a specialised decoder at his office which enables the graphs of blood pressure to be recorded and, for example, displayed visually.

Another feature of the apparatus shown in FIG. 1 gives an improvement in the quality of the electrocardiograms which are picked up and recorded. In order to avoid interferences (myograms) due to muscular artifacts, the electrocardiogram pick-up electrodes 2 and 3 only extend over approximately two thirds of the cavity receiving the patient's fingers or other parts of his hands; the other parts of the electrodes 2 and 3 indicated at 40 and 41 respectively are insulated from the electrodes 2 and 3, for example by a wall (not shown) and form earth electrodes which are connected to the electronic devices for processing the electrocardiogram picked up.

Moreover, the apparatus may comprise means for displaying the number of sequences already recorded; the recording memory enables several separate electrocardiogram recordings to be made and the display means enables the patient to know if it is still possible to make an electrocardiogram recording or if the memory capacity is full. The display means may conveniently be combined with a digital clock which displays the time and enables the date and time to be recorded simultaneously with the electrocardiograms. This display device can also, in a variant, indicate the number of recordings which may still be made.

We claim:

1. Portable apparatus for recording electrocardiograms from a patient's hand and comprising:
   a pocket-sized casing of generally parallelopipedal form:
   first and second electrode means on a surface of said casing for contacting at least parts of the respective hands of the patient for receiving electrocardiographic data; and
   resilient retaining means juxtapositioned with said electrode means for pressing said parts of the patient's hands into contact with said electrode means and maintaining said apparatus in position in the patient's hands, said resilient retaining means comprising first and second elastic bands extending over said first and second electrode means, respectively, said elastic bands having enlarged ends, said casing having grooves opening through slits to the exterior of a pair of opposing surfaces that lie generally normal to the surface containing said electrode means, said grooves receiving and retaining said enlarged ends of said bands with said bands extending through said slits, said slits having cutaway portions therealong by which said ends of said bands may be inserted in said grooves.

2. The apparatus as claimed in claim 1 wherein said first and second electrode means includes portions insulated from the remainder of the electrode means for forming a ground electrode for recording apparatus.

3. The apparatus as claimed in claim 1 wherein said first and second electrode means is further defined as having an area suitable for being contacted by at least the index fingers of the patient's hands.

4. The apparatus as claimed in claim 1 further including trigger means on the surface of said casing and actuatable by a portion of one of the patient's hands for triggering recording of an electrocardiogram.

5. The apparatus as claimed in claim 4 wherein said trigger means is further defined as positioned on said casing so as to be actuatable by the patient's index finger.

6. The apparatus as claimed in claim 4 wherein said trigger means is further defined as positioned on the casing so as to be actuatable by the patient's thumb.

7. The apparatus as claimed in claim 1 further including transducer means positioned on said casing for contacting at least a portion of one of the patient's hands for receiving blood pressure data.

8. The apparatus as claimed in claim 7 wherein said transducer means is further defined as positioned on said casing for being contacted by the patient's index finger.

* * * * *